United States Patent [19]

Lacks

[11] 4,325,383
[45] Apr. 20, 1982

[54] SYSTEM AND METHOD FOR MEASURING AND RECORDING BLOOD PRESSURE

[76] Inventor: Harold G. Lacks, 200 E. 64th St., New York, N.Y. 10021

[21] Appl. No.: 182,808

[22] Filed: Aug. 29, 1980

[51] Int. Cl.³ .............................................. A61B 5/02
[52] U.S. Cl. .................................... 128/677; 128/686
[58] Field of Search .............. 128/672, 677, 680, 681, 128/904, 682, 685

[56] References Cited

U.S. PATENT DOCUMENTS 3,132,643  5/1964  Baum et al.

OTHER PUBLICATIONS

*IBM Technical Disclosure Bulletin,* vol. 9, No. 6, Nov. 1966, pp. 558–559.

Primary Examiner—Robert W. Michell
Assistant Examiner—John C. Hanley
Attorney, Agent, or Firm—McAulay, Fields, Fisher, Goldstein & Nissen

[57] ABSTRACT

A system and method for measuring and recording intra-arterial systolic and diastolic blood pressures. The system encompasses a variable diameter sleeve which encompasses the patient's arm, and is adapted to be inflated to produce a predetermined maximum compression pressure and to decompress at a predetermined decompression rate. A telephone communication system is provided which is accessible by the patient whose blood pressure is to be detected. A stethoscope is connected to a pulse sensing device and to the telephone. A prerecorded voice count down device generates audible pressure readings beginning at the maximum compression pressure and decreasing at the predetermined decompression rate. The count down is in human understandable form and the device is operably connected to the telephone communication system. Since the prerecorded count down device counts down at the same rate as the decompression rate of the inflated sleeve, the actual systolic and diastolic blood pressure values can be easily determined.

3 Claims, 1 Drawing Figure

SYSTEM AND METHOD FOR MEASURING AND RECORDING BLOOD PRESSURE

BACKGROUND OF THE INVENTION

The present invention relates generally to systems and methods for measuring blood pressure, and more particularly to a system and method for measuring blood pressure relative to the predetermined decompression rate of a pressurized sleeve and the elapsed time from a predetermined intialization pressure to the systolic and diastolic blood pressures.

In the past, there have been various systems for measuring blood pressure. By way of example is U.S. Pat. No. 3,132,643 in which a blood pressure measurment system is illustrated. The blood pressure is measured in terms of time lapse between an electrocardiac signal and a consequent pressure pulse as measured at a pressure point in the body. However, this device requires the use of multiple sensors in measuring the travel time from the first sensor to the second sensor and converting that into a blood pressure reading.

The present invention provides a simple, economic means of measuring and recording the blood pressure of a patient using an enhanced device having a method of use similar to those devices already used in the field. Therefore, any patient not already skilled in taking blood pressures could easily be trained to use the device.

SUMMARY OF THE INVENTION

According to the present invention a system and method for measuring and recording an individual's systolic and diastolic blood pressures is presented.

The system comprises a variable diameter sleeve which fits about the arm of a patient for compressing the arm and then decompressing the arm at a known decompression rate, a sensing device for detecting the systolic and diastolic blood pressures, an amplifier device for transmitting the detected systolic and diastolic blood pressure signals to a processing device which computes the respective blood pressures relative to the decompression rate and the elapsed time from an initialization pressure to the systolic and diastolic pressure.

In one embodiment the sleeve is inflatable having a release valve allowing air pressure to be released from the sleeve and an escape valve which allows the sleeve to be pressurized to a predetermined maximum pressure. The sleeve is inflated until it reaches the maximum pressure as determined by the escape valve and at which time the flow of blood is occluded. A signal is transmitted from the processing device to open the release valve. The processing device is correlated with the rate of air release from the inflatable sleeve so that when a signal indicating the systolic pressure is received the amount of pneumatic pressure in the sleeve at that time can be recorded and when the signal indicating the diastolic pressure is received the amount of pneumatic pressure remaining in the sleeve is again recorded. Any medium for counting down at the decompression rate of the sleeve, such that at any time an accurate reading may be obtained can be utilized.

It is therefore an object of this invention to provide a system and method for measuring and recording blood pressure by correlating the decompression rate of a sleeve about the arm of a patient with the elapsed time from an initial reference pressure and the systolic and diastolic blood pressures.

It is an object of this invention to provide a system and method for measuring and recording blood pressure which eliminates human detection of systolic and diastolic pressures in correlation with a pressure gauge.

It is another object of this invention to provide a system and method for measuring and recording blood pressure which enables a patient's blood pressure to be taken from a remote location and transmitted to and recorded at a central location.

It is yet another object of this invention to provide a new and improved system and method for measuring and recording a blood pressure utilizing apparatus which any patient can easily learn to use.

In accordance with these and other objects which will be apparent hereinafter, the instant invention will now be described with particular reference to the accompanying drawings.

PREFERRED EMBODIMENT OF THE INVENTION

Figure 1:
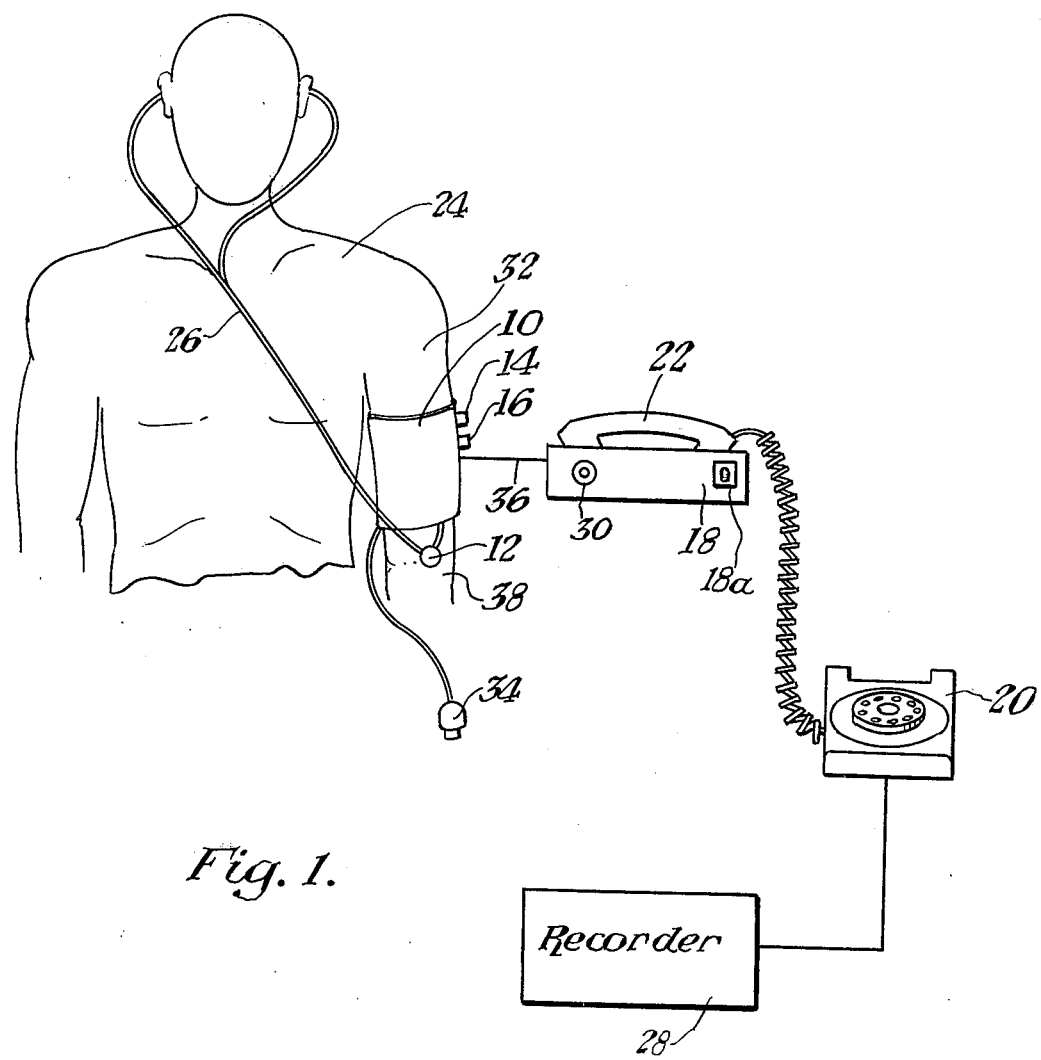
FIG. 1 is a general view of the system.

Referring now to FIG. 1 the invention is shown with the pneumatic sleeve or inflatable cuff 10 placed around the arm 32 of the patient 24. The sleeve 10 is inflatable to a predetermined volume of air (approximately 200 mm) in the cuff relative to the air pressure produced, regardless of the various circumferential measurements of the patients' arms by repeatedly squeezing bulb 34. The sleeve includes an escape valve 14, stethoscope fixture 12 and release valve 16. The amplifier 18 is connectable to an ordinary phone receiver 22 and includes a permanent on-off switch 18a and a second switch 30 to momentarily reactivate amplifier 18 when permanent switch 18a is off and to transmit an audible signal via the telephone 20 to the recorder 28. The stethoscope fixture 12 feeds heart sound to a first earphone the stethoscope 26 and also feeds sound from the amplifier 18 via line 36 a second earphone of the stethescope 26 enabling the user to listen for both sounds.

To operate the invention the proper phone number to the recorder 28 (such as a telephone answering machine player) is dialed on the phone 20 and the receiver 22 is connected to the amplifier 18. The pneumatic sleeve 10 is placed around the patient's arm 32 and inflated by pumping bulb 34. The sleeve 10 is continually inflated until the maximum pressure escape valve is activated and the proper air pressure is contained within the sleeve 10 to occlude the blood flow in the extremity 38. The amplifier 18 receives a signal from the recorder 28 and signals the patient to open the release valve 16. The recorder 28 has a prerecorded tape thereon which counts down from the predetermined maximum pressure to any desired minimum pressure at the rate of pressure release from the sleeve. It should also be noted that the manual methods could be replaced by having the recorder 28 emitting a special frequency tone at the time start is required. The tone would then activate sound sensing switches to open the release valve 16 and to turn the amplifier 18 to an off position.

Air in the sleeve 10 will escape therefrom at a predetermined rate through the release valve 16. The decrease in sleeve pressure is coincident with the countdown of device 28 but cannot be heard by user beacuse amplifier sound has been turned off. When the sleeve pressure descends through the heart pulse pressure in the arm 32 the patient senses the restart of heart pulse blood flow (systolic blood pressure) in the extremity 38 and depresses the second switch 30, which turns the amplifier on and enables the patient to hear the recorder 28 audibly play back the pressure reading corresponding to the systolic pressure reading. The patient may then record his systolic pressure in human understandable form.

Sleeve pressure will continue to decrease through the release valve 16 until the sleeve 10 relaxes around the arm and the sleeve pressure is no longer perturbated by the heart pulse blood flow into arm 32. At this point, the second switch 30 is again depressed turning the amplifier 18 on and again enabling the patient to hear the recorder 28 audibly play back the pressure reading corresponding to the diastolic reading. The patient may then record his diastolic pressure in human understandable form. Once the patient receives the blood pressures the phone receiver 22 is placed back in its normal position on the telephone 20 and the recorder 28 resets.

It should be noted that the amplifier 18 could be removed from the system and one line of the stethoscope 26 connected directly to the telephone reciever when the systolic and diastolic pressures are sensed enabling the patient to hear the readings from the recorder 28.

It should be noted that other prerecorded devices could be used to replace the recorder countdown device 28, and any sleeve that contracts about the arm could be used.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A system for measuring the systolic and diastolic blood pressure of a patient comprising:
    a pressure means connectable about an extremity of the patient for compression of the extremity to a predetermined maximum compression pressure and decompression of the extremity at a predetermined decompression rate;
    a telephone communication system including a telephone accessible by the patient;
    a stethoscope connected to a pulse sensing device and to said telephone; and
    a prerecorded voice countdown means for generating audible pressure readings from said maximum compression pressure at said predetermined decompression rate in human understandable form, operably connected to said telephone communications system.

2. A system for measuring the systolic and diastolic blood pressure of a patient as set forth in claim 1, further comprising:
    an amplifier means for engaging said telephone and amplifying said audible pressure readings; and
    said amplifier means having an input for feeding said stethoscope and at least one switch having an amplifier off position and an amplifier on position.

3. A method for measuring the systolic and diastolic blood pressure of a patient comprising the steps of:
    connecting a pressure means about an extremity of the patient;
    compressing the extremity with said pressure means to a predetermined maximum compressing pressure;
    starting decompression of the extremity at a predetermined decompression rate;
    starting a prerecorded voice countdown means which generates audible pressure readings starting from said maximum compression pressure at said decompression rate;
    detecting said systolic blood pressure;
    listening to said audible pressure reading at a first time corresponding to said systolic blood pressure reading;
    detecting said diastolic blood pressure; and
    listening to said audible pressure reading at a second time corresponding to said diastolic blood pressure reading.

* * * * *